United States Patent [19]

Mathur et al.

[11] Patent Number: 5,925,749

[45] Date of Patent: *Jul. 20, 1999

[54] CARBOXYMETHYL CELLULASE FROM *THERMOTOGA MARITIMA*

[75] Inventors: Eric J. Mathur, Carlsbad; David E. Lam, Harbor City, both of Calif.

[73] Assignee: Diversa Corporation, San Diego, Calif.

[*] Notice: This patent is subject to a terminal disclaimer.

[21] Appl. No.: 09/066,075

[22] Filed: Apr. 24, 1998

Related U.S. Application Data

[63] Continuation of application No. 08/518,615, Aug. 23, 1995.

[51] Int. Cl.$^6$ .............................. C07H 21/04; C07H 21/02
[52] U.S. Cl. ...................... 536/23.1; 536/23.2; 536/24.32
[58] Field of Search ........................... 435/252.3, 254.11, 435/320.1; 536/23.2, 24.32, 23.1

[56] References Cited

U.S. PATENT DOCUMENTS 5,420,029  5/1995  Gelfand et al. ......................... 435/194

OTHER PUBLICATIONS

Accession Q32472 on the N–Geneseq database. Submitted by Hayashi et al. Apr. 26, 1993.

Shima, S. et al. "Nucleotide sequence analysis of the endo–glucanase–encoding gene, ceICCD, of Clostridium cellulolyticum." Gene (Jul. 1991), vol. 104, No. 1, pp. 33–38.

Ooi et al., Expression of the Cellulase (F1–CM Case) Gene . . . , Biosci. Biotech. Biochem 57(11):1960–1961 (1993).

Ooi et al., Expression of the Cellulase (F1–CM Case) Gene . . . , Biosci. Biotech. Biochem 58(5):954–956 (1994).

Gilbert et al., Evidence of Multiple Carboxymethyl Cellulase Genes . . . , Molecular Gen Genetics 210:551–556 (1987).

Bronnenmeier et al., Purification of *Thermatoga Maritima* Enzymes for the Degradation of Cellulosic Materials; Apr. 1995; vol. 61, No. 4; pp. 1399–1407.

*Primary Examiner*—Robert A. Wax
*Assistant Examiner*—Bradley S. Mayhew
*Attorney, Agent, or Firm*—Fish & Richardson P.C.

[57] ABSTRACT

A purified thermostable enzyme is derived from the eubacterium *T. maritima*. The enzyme has a molecular weight as determined by gel electrophoresis of about 35 kilodaltons and has cellulase activity. The enzyme can be produced from native or recombinant host cells and can be used to aid in the digestion of cellulose where desired.

4 Claims, 3 Drawing Sheets

```
ATG GGT GTT GAT CCT TTT GAA AGG AAC AAA ATA TTG GGA AGA GGC ATT AAT ATA
 M   G   V   D   P   F   E   R   N   K   I   L   G   R   G   I   N   I

GGA AAT GCG CTT GAA GCA CCA AAT GAG GGA GAC TGG GGA GTG GTG ATA AAA GAT
 G   N   A   L   E   A   P   N   E   G   D   W   G   V   V   I   K   D

GAG TTC GAC ATT ATA AAA GAA GCC GGT TTC CCT CCT TAT CAT GTT CGA ATT CCA ATA
 E   F   D   I   I   K   E   A   G   F   P   P   Y   H   V   R   I   P   I

AGA TGG AGT ACG CAC GCT TAC GCG TTT CCT TAT AAA ATC ATG GAA GGA CTG GCT GTT
 R   W   S   T   H   A   Y   A   F   P   Y   K   I   M   E   G   L   A   V

TTC AAA AGA GTG GAT GAA GTG ATA AAC GGA GCC CTG AAA AGA CCA GAA CAC AAG
 F   K   R   V   D   E   V   I   N   G   A   L   K   R   P   E   H   K

GCT ATA AAT ATT CAT CAC TAC GAG TTA ATG AAT GAT CCA TAT AAA GAC TAT CCC
 A   I   N   I   H   H   Y   E   L   M   N   D   P   Y   K   D   Y   P

GAA AGA TTT CTT GCT CTT TGG AAA CAA ATT GCT GAT CGT TAT AAA GAC TAT CCC
 E   R   F   L   A   L   W   K   Q   I   A   D   R   Y   K   D   Y   P
```

```
GAA AAA AAG AAA AAT TGG TTC
 E   K   K   K   N   W   F

ACT TGG CAC CTG CCT TTG AAT
 T   W   H   L   P   L   N

CTA AAT ACT TCT TTC GGA TTT
 L   N   T   S   F   G   F

TTT GAA ATA GTC GAA AGA ATA
 F   E   I   V   E   R   I

TTT CTG ATT CCA TTT AAG GAA
 F   L   I   P   F   K   E

GAA CTT ATA AAA ACC TGG TGG
 E   L   I   K   T   W   W

ATT GAG GGC TGG CAT GGA TCA
 I   E   G   W   H   G   S

CTG GAA ACA GAA CAA AGA GAA
 L   E   T   E   Q   R   E

AAT GCT GCT AAA TCT AAG TGG
 N   A   A   K   S   K   W

GAA CTA GAA AAT CCA TGG TTG
 E   L   E   N   P   W   L

CCT AAA TGG TCT GAT GTG GAA
 P   K   W   S   D   V   E

CAC GTT GGG ATA GAT GAG GAG
 H   V   G   I   D   E   E

GGA ATA GGT GTT GAT TGG ATA
 G   I   G   V   D   W   I

AAT AGA ATA ACA CAG CAG TAC
 N   R   I   T   Q   Q   Y

CTT TCA TCT CAC AAA GAT ATT
 L   S   S   H   K   D   I

ACT ATT GCC TAC AAA GAT TAC
 T   I   A   Y   K   D   Y

CCG GAC CTT TAC AAC AGA ATA
 P   D   L   Y   N   R   I

GAA AAA GAA TAC AAA GAA GGT
 E   K   E   Y   K   E   G
```

```
GAG TTT GGT GCC TAC AGA AAA GCT GAC CTT GAA TCA AGA ATA AAA TGG ACC TCC
 E   F   G   A   Y   R   K   A   D   L   E   S   R   I   K   W   T   S

TTT GTC GTT CGC GAA ATG GAG AAA AGG AGA CTG AGA TGG AGC TGG GCA TAC TGG GAA TTT
 F   V   V   R   E   M   E   K   R   R   L   R   W   S   W   A   Y   W   E   F

TGT TCC GGT TTT GGT GTT TAT GAT ACT CTG AGA AAA ACC TGG AAT AAA GAT CTT
 C   S   G   F   G   V   Y   D   T   L   R   K   T   W   N   K   D   L

TTA GAA GCT TTA ATA GGA GGA GAT AGC ATT GAA TAA
 L   E   A   L   I   G   G   D   S   I   E   *
```

FIG. 1C

CARBOXYMETHYL CELLULASE FROM *THERMOTOGA MARITIMA*

This application is a Continuation application of U.S. patent application Ser. No. 08/518,615 filed on Aug. 23, 1995.

This invention relates to newly identified polynucleotides, polypeptides encoded by such polynucleotides, the use of such polynucleotides and polypeptides, as well as the production and isolation of such polynucleotides and polyp eptides. More particularly, the polypeptide of the present invention has been putatively identified as an endoglucanase and in particular an enzyme having carboxymethyl cellulase activity, sometimes hereinafter referred to as "CMCase".

Cellulose, a fibrous, tough, water-insoluble substance is found in the cell walls of plants, particularly, in stalks, stems, trunks and all the woody portions of plant tissues. Cellulose constitutes much of the mass of wood, and cotton is almost pure cellulose. Because cellulose is a linear, unbranched homopolysaccharide of 10,000 to 15,000 D-glucose units, it resembles amylose and the main chains of glycogen. But there is a very important difference; in cellulose, the glucose residues have the beta configuration, whereas in amylose, amylopectin and glycogen the glucose is in the alpha configuration. The glucose residue s in cellulose are linked by (beta 1→4) glycosidic bonds. This difference gives cellulose and amylose very different 3-dimensional structures and physical properties.

Cellulose cannot be used by most animals as a source of stored fuel, because the (beta 1→4) linkages of cellulose are not hydrolyzed by alpha-amylases. Termites readily digest cellulose but only because their intestinal tract harbors a symbiotic microorganism, trichonympha, which secretes cellulase, an enzyme that hydrolyzes (beta 1→4) linkages between glucose units. The only vertebrates able to use cellulose as food are cattle and other ruminant animals (sheep, goats, camels and giraffes). The extra stomachs "rumens" of these animals teem with bacteria and protists that secrete cellulase.

The enzymatic hydrolysis of cellulose is considered to require the action of both endoglucanases (1,4-beta-D-glucan glucanohydrolase) and exoglucanases (1,4-beta-D-glucan cellobiohydrolase). A synergistic interaction of these enzymes is necessary for the complete hydrolysis of crystalline cellulose. (Caughlin, M. P., Genet. Eng. Rev., 3:39–109 (1985). For the complete degradation of cellulose (cellulose to glucose), β-glucosidase might be required if the "exo" enzyme does not release glucose. 1,4-β-d-Glucan glucohydrolase is another type of "exo" cellulase.

Thermophilic bacteria have received considerable attention as sources of highly active and thermostable cellulolytic and Xynalytic enzymes (Bronneomeier, K. and Staudenbauer, W. L., D. R. Woods (Ed.), The Clostridia and Biotechnology, Butterworth Publishers, Stoneham, Mass. (1993), 22,34). Recently, the most extremely thermophilic organotrophic eubacteria presently known have been isolated and characterized. These bacteria, which belong to the genus thermotoga, are fermentative microorganisms metabolizing a variety of carbohydrates (Huber, R. and Stetter, K. O., in Ballows, et al., (Ed.), the procaryotes, 2nd Ed., Springer-Verlaz, New York, pgs. 3809–3819 (1992)).

In Huber et al., 1986, Arch. Microbiol. 144:324–333, the isolation of the bacterium *Thermotoga maritima* is described. *T. maritima* is a eubacterium that is strictly anaerobic, rod-shaped, fermentative, hyperthermophilic, and grows between 55° C. and 90° C., with an optimum growth temperature of about 80° C. This eubacterium has been isolated from geothermally heated sea floors in Italy and the Azores. *T. maritima* cells have a sheath-like structure and monotrichous flagellation. *T. maritima* is classified in the eubacterium kingdom by virtue of having murein and fatty acid-containing lipids, diphtheria-toxin-resistant elongation factor 2, an RNA polymerase subunit pattern, and sensitivity to antibiotics.

The polynucleotide sequence and polypeptide encoded thereby of the present invention has been putatively identified as an endoglucanase having carboxymethyl cellulose activity.

In accordance with one aspect of the present invention, there is provided a novel enzyme, as well as active fragments, analogs and derivatives thereof.

In accordance with another aspect of the present invention, there are provided isolated nucleic acid molecules encoding an enzyme of the present invention including mRNAs, DNAs, cDNAs, genomic DNAs as well as active analogs and fragments of such enzymes.

In accordance with yet a further aspect of the present invention, there is provided a process for producing such polypeptide by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for utilizing such enzyme, or polynucleotide encoding such enzyme for degradation of cellulose for the conversion of plant biomass into fuels and chemicals, may also be used in detergents, the textile industry, in animal feed, in waste treatment, and in the fruit juice/brewing industry for the clarification and extraction of juices.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1A, FIG. 1B and FIG. 1C illustrate the full-length DNA and corresponding deduced amino acid sequence of the enzyme of the present invention. Sequencing was performed using a 378 automated DNA sequencer (Applied Biosystems, Inc.).

The present invention provides a purified thermostable enzyme that catalyzes the hydrolysis of the beta 1,4 glycosidic bonds in cellulose to thereby degrade cellulose. The purified enzyme is a carboxymethyl cellulase from *T. maritima* which is a thermophilic eubacteria which grows in temperatures up to 90° C. The organism is strictly anaerobic, rod-shaped and fermentative, and grows between 55 and 90° C. (optimally at 80° C.). *Thermotoga maritima* is a representative of the genus Thermotoga.

In a preferred embodiment, the CMCase enzyme of the present invention has a molecular weight of about 35 kilodaltons as measured by SDS-PAGE gel electrophoresis and an inferred molecular weight from the nucleotide sequence of the gene. This purified enzyme may be used to catalyze the enzymatic degradation of cellulose where desired.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences. A "promoter sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

In accordance with an aspect of the present invention, there is provided an isolated nucleic acid (polynucleotide) which encodes for the mature enzyme having the deduced amino acid sequence of FIG. 1 (SEQ ID NO:2) or for the mature enzyme encoded by the cDNA contained in the pBluescript II clone deposited as ATCC Deposit No. 97245.

This invention, in addition to the isolated nucleic acid molecules encoding a CMCase enzyme, also provides substantially similar sequences. Isolated nucleic acid sequences are substantially similar if: (i) they are capable of hybridizing under stringent conditions, hereinafter described, to SEQ ID NO:1; (ii) or they encode DNA sequences which are degenerate to SEQ ID NO:1. Degenerate DNA sequences encode the amino acid sequence of SEQ ID NO:2, but have variations in the nucleotide coding sequences. As used herein, substantially similar refers to the sequences having similar identity to the sequences of the instant invention. The nucleotide sequences that are substantially the same can be identified by hybridization or by sequence comparison. Enzyme sequences that are substantially the same can be identified by one or more of the following: proteolytic digestion, gel electrophoresis and/or microsequencing.

The polynucleotide of this invention was originally recovered from a genomic gene library derived from the organism *Thermotoga maritima*, as hereinafter described. It contains an open reading frame encoding a protein of 317 amino acid residues. The protein exhibits the highest degree of homology to endo-1,4-beta-glucanase D from clostridium cellulolyticum with 36% identity at the amino acid level, and 17.2% identity at the DNA level.

One means for isolating a nucleic acid molecule encoding a CMCase enzyme is to probe a genomic gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO:1 (i.e., comprising at least 15 contiguous nucleotides).

With respect to nucleic acid sequences which hybridize to specific nucleic acid sequences disclosed herein, hybridization may be carried out under conditions of reduced stringency, medium stringency or even stringent conditions (e.g., conditions represented by a wash stringency of 0.5× SSC and 0.1% SDS at a temperature of 20 or 30° below the melting temperature of the probe, or even conditions represented by a wash stringency of 0.1×SSC and 0.1% SDS at a temperature of 10° below the melting temperature of the DNA sequence to target DNA) in a standard hybridization assay. See J. Sambrook et al., Molecular Cloning, A Laboratory Manual (2d Ed. 1989) (Cold Spring Harbor Laboratory).

It Is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

The coding sequence for the CMCase enzyme of the present invention was identified by preparing a *T. maritima* genomic DNA library and screening the library for the clones having CMCase activity. Such methods for constructing a genomic gene library are well-known in the art. One means comprises shearing DNA isolated from *T. maritima* by physical disruption. A small amount of the sheared DNA is checked on an agarose gel to verify that the majority of the DNA is in the desired size range (approximately 3–6 kb). The DNA is then blunt ended using Mung Bean Nuclease, incubated at 37° C. and phenol/chloroform extracted. The DNA is then methylated using Eco RI Methylase. Eco RI linkers are then ligated to the blunt ends through the use of T4 DNA ligase and incubation at 4° C. The ligation reaction is then terminated and the DNA is cut-back with Eco RI restriction enzyme. The DNA is then size fractionated on a sucrose gradient following procedures known in the art, for example, Maniatis, T., et al., *Molecular Cloning*, Cold Spring Harbor Press, New York, 1982, which is hereby incorporated by reference in its entirety.

A plate assay is then performed to get an approximate concentration of the DNA. Ligation reactions are then performed and 1 μl of the ligation reaction is packaged to construct a library. The library is then amplified.

The gene and gene products of the present invention may also be used as a probe to isolate other nucleic acid sequences and other enzymes upon isolation and expression, which may then be measured for retention of biological activity characteristic to the enzyme of the present invention, for example, in an assay for detecting enzymatic CMCase activity. Such enzymes include truncated forms of CMCase, and variants such as deletion and insertion variants.

An example of such an assay is an assay for the detection of endogluconase activity based on specific interaction of direct dyes such as Congo red with polysaccharides. This colorant reacts with beta-1,4-glucans causing a visible red shift (Wood, P. J., Carbohydr. Res., 85:271 (1980) and Wood, P. J., Carbohydr. Res., 94:c19 (1981)). The preferred substrate for the test is carboxymethylcellulose (CMC) which can be obtained from different sources (Hercules Inc., Wilmington, Del., Type 4M6F or Sigma Chemical Company, St. Louis, Mo., Medium Viscosity). The CMC is incorporated as the main carbon sources into a minimal agar medium in quantities of 0.1–1.0%. The microorganisms can be screened directly on these plates, but the replica plating technique from a master plate is preferable since the visualization of the activity requires successive floodings with the reagents, which would render the reisolation of active colonies difficult. Such endoglucanase-producing colonies are detectable after a suitable incubation time (1–3 days depending on the growth), by flooding the plate with 10 ml of a 0.1% aqueous solution of Congo Red. The coloration is terminated after 20 minutes by pouring off the dye and flooding the plates with 10 ml of 5M NaCl solution (commercial salt can be used). After an additional 20 minutes, the salt solution is discarded and endoglucanase activity is revealed by a pale-orange zone around the active microorganisms. In some cases, these zones can be enhanced by treating the plates with 1 N acetic acid, causing the dye to change its color to blue.

The same technique can be used as a cup-plate diffusion assay with excellent sensitivity for the determination of CMCase activity in culture filtrates or during enzyme purification steps (Carger, J. H., Anal. Biochem., 153:75 (1986)). See generally, Methods for Measuring Cellulase Activities, Methods in Enzymology, Vol. 160, pgs. 87–116.

The enzyme of the present invention has enzymatic activity with respect to the hydrolysis of the beta 1,4 glycosidic bonds in carboxymethylcellulose, since the halos discussed above are shown around the colonies.

The polynucleotide of the present invention may be in the form of DNA which DNA includes CDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequence shown in FIG. 1 (SEQ ID NO:1) or that of the deposited clone or may be a different coding sequence which coding sequence, as a result of the redundancy or degeneracy of the genetic code, encodes the same mature enzyme as the DNA of FIG. 1 (SEQ ID NO:1) or the deposited DNA.

The polynucleotide which encodes for the mature enzyme of FIG. 1 (SEQ ID NO:2) or for the mature enzyme encoded by the deposited cDNA may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzyme having the deduced amino acid sequence of FIG. 1 (SEQ ID NO:2) or the enzyme encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 (SEQ ID NO:2) or the same mature enzyme encoded by the cDNA of the deposited clone as well as variants of such polynucleotides which variants encode for a fragment, derivative or analog of the enzyme of FIG. 1 (SEQ ID NO:2) or the enzyme encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. The enzyme having a leader sequence is a preprotein and may have the leader sequence cleaved by the host cell to form the mature form of the enzyme. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and a presequence (leader sequence).

Fragments of the full length gene of the present invention may be used as a hybridization probe for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe.

Labeled oligonucleotides having a sequence complementary to that of the gene of the present invention are used to screen a library of genomic DNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIG. 1 (SEQ ID NO:1) or the deposited DNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the enzyme of SEQ ID NO:2 as well as fragments thereof, which fragments have at least 30 bases and preferably at least 50 bases and to enzymes encoded by such polynucleotides.

The deposit(s) referred to herein will be maintained under the terms of the Budapest Treaty on the International Recognition of the Deposit of Micro-organisms for purposes of Patent Procedure. These deposits are provided merely as a convenience to those of skill in the art and are not an admission that a deposit is required under 35 U.S.C. §112. The sequence of the polynucleotides contained in the deposited materials, as well as the amino acid sequence of the enzymes encoded thereby, are incorporated herein by reference and are controlling in the event of any conflict with any description of sequences herein. A license may be required to make, use or sell the deposited materials, and no such license is hereby granted.

The present invention further relates to a enzyme which has the deduced amino acid sequence of FIG. 1 (SEQ ID NO:2) or which has the amino acid sequence encoded by the deposited DNA, as well as fragments, analogs and derivatives of such enzyme.

The terms "fragment," "derivative" and "analog" when referring to the enzyme of FIG. 1 (SEQ ID NO:2) or that encoded by the deposited DNA, means a enzyme which retains essentially the same biological function or activity as such enzyme. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The fragment, derivative or analog of the enzyme of FIG. 1 (SEQ ID NO:2) or that encoded by the deposited DNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzyme of SEQ ID NO:2 (in particular the mature enzyme) as well as enzymes which have at least 70% similarity (preferably at least 70% identity) to the enzyme of SEQ ID NO:2 and more preferably at least 90% similarity (more preferably at least 90% identity) to the enzyme of SEQ ID NO:2 and still more preferably at least 95% similarity (still more preferably at least 95% identity) to the enzyme of SEQ ID NO:2 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Bacillus subtilis*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pD10, psiX174, pBluescript II KS, pNH8A, pNH16a, pNH18A, pNH46A (Stratagene); ptrc99a, pKK223-3, pKK233-3, pDR540, pRIT5 (Pharmacia); Eukaryotic: pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

The enzyme of this invention may be employed for any purpose in which such enzyme activity is necessary or desired. In a preferred embodiment the enzyme is employed for catalyzing the hydrolysis of cellulose. The degradation of cellulose may be used for the conversion of plant biomass into fuels and chemicals.

The enzyme of the present invention may also be employed in detergents, the textile industry, in animal feed, in waste treatment and in the fruit juice/brewing industry for the clarification and extraction of juices.

In a preferred embodiment, the enzyme of the present invention is a thermostable enzyme which is stable to heat and is heat resistant and catalyzes the enzymatic hydrolysis of cellulose, i,e., the enzyme is able to renature and regain activity after brief (i.e., 5 to 30 seconds) exposure to temperatures of 80° C. to 105° C. and has a temperature optimum of above 60° C.

The enzymes, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", *Mehfods in enzymology*, Vol 160, pp. 87–116, which is hereby incorporated by reference in its entirety.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of CMCase

A *T. maritima* genomic library was constructed in the Lambda ZapII® cloning vector (Stratagene Cloning Systems), and mass excision was performed according to the manufacturers protocol to yield a gene library in the pBluescript cloning vector. The pBluescript library was screened in SOLR *E. Coli* cells (Stratagene) for CMCase activity and a positive clone was identified and isolated. This clone was used to innoculate an overnight culture of Luria Broth liquid medium as per Ausubel, F. M., et al., Short Protocols in Molecular Biology, 2d Ed., Harvard Medical School (1992). The plasmid DNA was isolated from the overnight culture using an alkaline lysis mini-prep protocol as per Maniatis, T., et al., Molecular Cloning, Cold Spring Harbor Press, New York (1982). Mini-prep DNA was then used to transform competent *E. coli* cells, XL1 blue (Stratagene) according to the manufacturer's protocol. A single clone was then used to innoculate a 100 ml overnight culture of Luria Broth liquid medium and plasmid DNA was isolated from this overnight using midi-prep procedure according to the manufacturer's protocol (Qiagen). The midi-prep plasmid DNA was partially sequenced with an ABI 377 and a putative open reading frame was idnetified within the sequenced region. The sequence information was used in the generation of primer sequences which were subsequently used to PCR amplify the target gene encoding the CMCase activty. The primer sequences used were as follows:

5'TTATTGCGGCCGCTTAAGGAG-GAAAAAATTATGGGTGTTGATCCTTTTGAA 3' (SEQ, ID NO:3) and 5'TTATTGGATCCGAAGGT-TGAAACCACGCCATCT3' (SEQ ID NO:4).

The amplification product was subcloned into the pBluescript II cloning vector (Stratagene). The plasmid clone was transformed in to XL1 Blue cells again for verification. The plasmid clone contains the DNA encoding the CMCase enzyme of the present invention as shown in FIG. 1 and deposited as ATCC No. 97245.

A pBLuescript II clone containing the DNA encoding the enzyme of the present invention may be obtained from the ATCC, ATCC Deposit No. 97245. This pBluescript II clone containing the DNA of the present invention is used to transform *E. coli* XL1 Blue cells and the *E. coli* XL1 Blue cells are used to innoculate innoculate a 5 ml overnight culture of Luria Broth liquid medium. The 5 ml culture was aliquoted into 1 ml aliquots, and each aliquot was used to innoculate 1 liter of 5×LB culture media. Cells were grown overnight in five 2-liter shake flasks at 37° C. Each one liter cell culture pellet was resuspended in 150 ml of 25 mM Tris, pH 8.0 and then spun at 4K rpm for 10 minutes at 4° C. The resulting pellet was resuspended in 5 ml of 25 mM Tris, pH 8.0, and sonicated with a microsonicator tip 10 times at 30 second intervals. The cell debris was spun out in a SS-34 rotor at 12K rpms for 10 minutes at 4° C. The resulting supernatant was then brought up to 10% ethanol and incubated at 75° C. for 20 minutes. The flocculated proteins were spun out in an SS-34 rotor at 10K rpms for 10 minutes at 4° C. The resultant supernatant was then filtered through a 0.22 micron filter and applied to a weak anion exchange column (Poros, PI). The column was eluted with a 250, 500, 800 mM NaCl step in a 10 mM Tris Base/10 mM Bis Tris Propane buffer at pH 8.0 (anion buffer). The active CMCase fraction came off at the 250 mM step. This fraction was then diluted with the anion buffer to a concentration of 50 mM. It was then applied to a strong anion exchange column (Poros, HQ) and the column was eluted with a 10 column volume gradient from 50 to 250 mM NaCl using anion buffer. A one band fraction of a 35 kD cellulase comes off in this gradient at approximately 150 mM NaCl.

Numerous modifications and variations of the present invention are possible in light of the above teachings and, therefore, within the scope of the appended claims, the invention may be practiced otherwise than as particularly described.

What is claimed is:

1. An isolated oligonucleotide comprising 30 contiguous polynucleotides from the polynucleotide set forth in SEQ ID No:1.

2. The oligonucleotide of claim 1, wherein the oligonucleotide is DNA.

3. The oligonucleotide of claim 1, wherein the probe further comprises a detectable isotopic label.

4. The oligonucleotide of claim 1, wherein the oligonucleotide further comprises a detectable non-isotopic label selected from the group consisting of a fluorescent molecule, a chemiluminescent molecule, an enzyme, a cofactor, an enzyme substrate, and a hapten.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 954 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:1:

```
ATGGGTGTTG ATCCTTTTGA AAGGAACAAA ATATTGGGAA GAGGCATTAA TATAGGAAAT    60
GCGCTTGAAG CACCAAATGA GGGAGACTGG GGAGTGGTGA TAAAAGATGA GTTCTTCGAC   120
ATTATAAAAG AAGCCGGTTT CTCTCATGTT CGAATTCCAA TAAGATGGAG TACGCACGCT   180
TACGCGTTTC CTCCTTATAA AATCATGGAT CGCTTCTTCA AAAGAGTGGA TGAAGTGATA   240
AACGGAGCCC TGAAAAGAGG ACTGGCTGTT GCTATAAATA TTCATCACTA CGAGGAGTTA   300
ATGAATGATC CAGAAGAACA CAAGGAAAGA TTTCTTGCTC TTTGGAAACA AATTGCTGAT   360
CGTTATAAAG ACTATCCCGA AACTCTATTT TTTGAAATTC TGAATGAACC TCACGGAAAT   420
CTTACTCCGG AAAAATGGAA TGAACTGCTT GAGGAAGCTC TAAAAGTTAT AAGATCAATT   480
GACAAAAAGC ACACTATAAT TATAGGCACA GCTGAATGGG GGGTATATC TGCCCTTGAA   540
AAACTGTCTG TCCCAAAATG GAAAAAAAT TCTATAGTTA CAATTCACTA CTACAATCCT   600
TTCGAATTTA CCCATCAAGG AGCTGAGTGG GTGGAAGGAT CTGAGAAATG GTTGGGAAGA   660
AAGTGGGGAT CTCCAGATGA TCAGAAACAT TTGATAGAAG AATTCAATTT TATAGAAGAA   720
TGGTCAAAAA AGAACAAAAG ACCAATTTAC ATAGGTGAGT TTGGTGCCTA CAGAAAAGCT   780
GACCTTGAAT CAAGAATAAA ATGGACCTCC TTTGTCGTTC GCGAAATGGA GAAAAGGAGA   840
TGGAGCTGGG CATACTGGGA ATTTGTTCC GGTTTTGGTG TTTATGATAC TCTGAGAAAA   900
ACCTGGAATA AAGATCTTTT AGAAGCTTTA ATAGGAGGAG ATAGCATTGA ATAA         954
```

(2) INFORMATION FOR SEQ ID NO:2:

(i) SEQUENCE CHARACTERISTICS:
        (A) LENGTH: 317 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

```
Met Gly Val Asp Pro Phe Glu Arg Asn Lys Ile Leu Gly Arg Gly Ile
              5                  10                  15

Asn Ile Gly Asn Ala Leu Glu Ala Pro Asn Glu Gly Asp Trp Gly Val
         20                  25                  30

Val Ile Lys Asp Glu Phe Phe Asp Ile Ile Lys Glu Ala Gly Phe Ser
     35                  40                  45

His Val Arg Ile Pro Ile Arg Trp Ser Thr His Ala Tyr Ala Phe Pro
 50                  55                  60

Pro Tyr Lys Ile Met Asp Arg Phe Lys Arg Val Asp Glu Val Ile
 65                  70                  75                  80

Asn Gly Ala Leu Lys Arg Gly Leu Ala Val Ala Ile Asn Ile His
                 85                  90                  95

Tyr Glu Glu Leu Met Asn Asp Pro Glu Glu His Lys Glu Arg Phe Leu
                100                 105                 110

Ala Leu Trp Lys Gln Ile Ala Asp Arg Tyr Lys Asp Tyr Pro Glu Thr
```

-continued

```
                  115                 120                 125
Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Ile Gly Thr Ala Glu Trp Gly Gly Ile
                165                 170                 175

Ser Ala Leu Glu Lys Leu Ser Val Pro Lys Trp Glu Lys Asn Ser Ile
                180                 185                 190

Val Thr Ile His Tyr Tyr Asn Pro Phe Glu Phe Thr His Gln Gly Ala
                195                 200                 205

Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
                260                 265                 270

Val Arg Glu Met Glu Lys Arg Arg Trp Ser Trp Ala Tyr Trp Glu Phe
    275                 280                 285

Cys Ser Gly Phe Gly Val Tyr Asp Thr Leu Arg Lys Thr Trp Asn Lys
290                 295                 300

Asp Leu Leu Glu Ala Leu Ile Gly Gly Asp Ser Ile Glu
305                 310                 315
```

(2) INFORMATION FOR SEQ ID NO:3:

(i) SEQUENCE CHARACTERISTICS:
        (A) LENGTH: 51 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

TTATTGCGGC CGCTTAAGGA GGAAAAAATT ATGGGTGTTG ATCCTTTTGA A    51

(2) INFORMATION FOR SEQ ID NO:4:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

TTATTGGATC CGAAGGTTGA AACCACGCCA TCT    33